United States Defensive Publication [19] (H) [11] T105,702

Lestina [43] Aug. 6, 1985

[54] NONDIFFUSIBLE PHOTOGRAPHIC COUPLERS AND PHOTOGRAPHIC ELEMENTS AND PROCESSES EMPLOYING SAME

[76] Inventor: Gregory J. Lestina, Kodak Park Works, Rochester, N.Y. 14650

[21] Appl. No.: 613,993

[22] Filed: May 25, 1984

Related U.S. Application Data

[60] Continuation of Ser. No. 474,372, Mar. 11, 1983, abandoned, which is a division of Ser. No. 366,885, Apr. 18, 1982, Pat. No. 4,443,536, which is a continuation-in-part of Ser. No. 296,086, Aug. 26, 1981, abandoned.

[51] Int. Cl.[3] ..... C07D 249/08

[52] U.S. Cl. ..... 548/262

[57] ABSTRACT

Photographic couplers comprising a coupler moiety and a ballast moiety have advantageous properties when the ballast moiety is terminated with a hydroxyphenylsulfonyl or hydroxyphenylsulfinyl group. The couplers are useful in photographic emulsions and element.

1 Claim, No Sheets Drawing,

55 Pages Specification

The file of this unexamined application may be inspected and copies thereof may be purchased (849 O.G. 1221, Apr. 9, 1968).